(12) United States Patent
Chen et al.

(10) Patent No.: US 11,002,704 B2
(45) Date of Patent: May 11, 2021

(54) BIOSENSOR DEVICES AND METHODS OF FORMING THE SAME

(71) Applicant: Taiwan Semiconductor Manufacturing Comany Limited, Hsinchu (TW)

(72) Inventors: Tung-Tsun Chen, Hsinchu (TW); Chien-Kuo Yang, Taipei (TW); Jui-Cheng Huang, Hsinchu (TW); Mark Chen, Hsinchu (TW); Ta-Chuan Liao, Taichung (TW); Cheng-Hsiang Hsieh, Taipei (TW)

(73) Assignee: Taiwan Semiconductor Manufacturing Company Limited, Hsinchu (TW)

( * ) Notice: Subject to any disclaimer, the term of this patent is extended or adjusted under 35 U.S.C. 154(b) by 275 days.

(21) Appl. No.: 15/252,661

(22) Filed: Aug. 31, 2016

(65) Prior Publication Data

US 2018/0059050 A1 Mar. 1, 2018

(51) Int. Cl.
| | |
|---|---|
| *G01N 27/414* | (2006.01) |
| *G01N 33/543* | (2006.01) |
| *H01L 21/306* | (2006.01) |
| *H01L 21/311* | (2006.01) |
| *H01L 29/06* | (2006.01) |
| *H01L 29/08* | (2006.01) |
| *H01L 29/10* | (2006.01) |

(Continued)

(52) U.S. Cl.
CPC ... *G01N 27/4145* (2013.01); *G01N 33/54373* (2013.01); *H01L 21/30604* (2013.01); *H01L 21/31111* (2013.01); *H01L 29/0649* (2013.01); *H01L 29/0684* (2013.01); *H01L 29/0847* (2013.01); *H01L 29/1033* (2013.01); *H01L 29/42356* (2013.01); *H01L 29/4916* (2013.01); *G01N 27/4148* (2013.01)

(58) Field of Classification Search
CPC .......... G01N 27/4148; G01N 33/54373; H01L 21/30604; H01L 21/31111; H01L 29/0649; H01L 29/0684; H01L 29/0847; H01L 29/1033; H01L 29/42356; H01L 29/4916

See application file for complete search history.

(56) References Cited

U.S. PATENT DOCUMENTS

| | | | | |
|---|---|---|---|---|
| 4,636,827 A | * | 1/1987 | Rudolf | H01L 29/7881 204/416 |
| 2006/0197118 A1 | * | 9/2006 | Migliorato | G01N 33/54373 257/253 |

OTHER PUBLICATIONS

Tsukada, K., et al. "An integrated micro multi-ion sensor using platinum-gate field-effect transistors." Solid-State Sensors and Actuators, 1991. Digest of Technical Papers, Transducers'91., 1991 International Conference on. IEEE, 1991.*

(Continued)

*Primary Examiner* — Robert J Eom
(74) *Attorney, Agent, or Firm* — Jones Day (57) ABSTRACT

Biosensor devices and methods of forming the same are provided. A cavity is formed in a substrate and is configured to receive one or more charged molecules. A transistor is formed in the substrate and includes a source region, a drain region, and a channel region that are spatially separated from the cavity in a lateral direction. A gate of the transistor is disposed below the cavity and extends between the cavity and the source, drain, and channel regions. A voltage potential of the gate is based on a number of the charged molecules in the cavity.

20 Claims, 11 Drawing Sheets

(51) Int. Cl.
*H01L 29/423* (2006.01)
*H01L 29/49* (2006.01)

(56) References Cited

OTHER PUBLICATIONS

Kim, Dong-Sun, et al. "An extended gate FET-based biosensor integrated with a Si microfluidic channel for detection of protein complexes." Sensors and Actuators B: Chemical 117.2 (2006): 488-494.*

* cited by examiner

BIOSENSOR DEVICES AND METHODS OF FORMING THE SAME

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and MEMS.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Figure 1A:
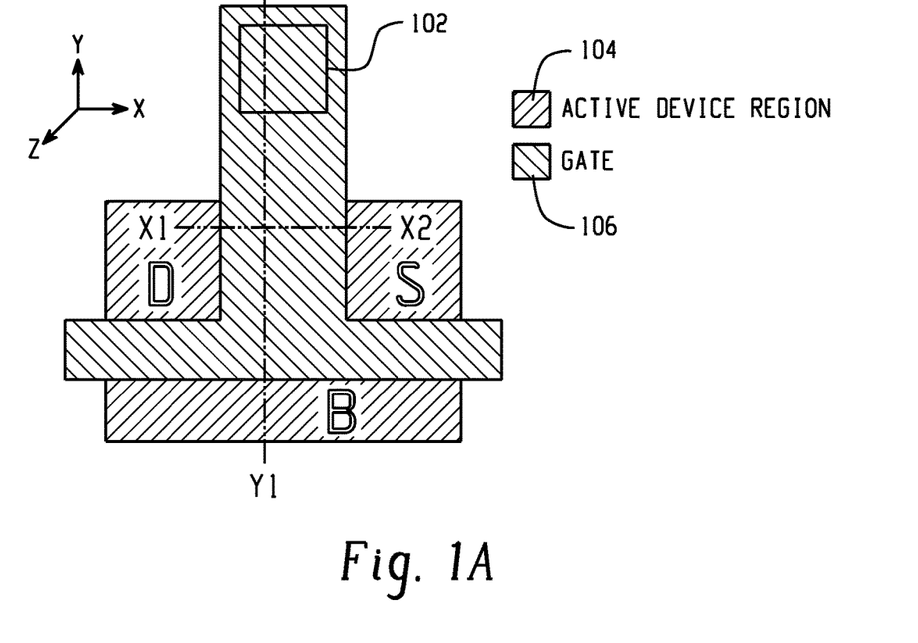
FIGS. 1A-1F depict example biosensor devices, in accordance with some embodiments.

FIGS. 1A-1F depict example biosensor devices, in accordance with some embodiments. Specifically, FIG. 1A depicts a top-down view of an example biosensor device and includes a cutline X1-X2 extending in an x-direction and a cutline Y1-Y2 extending in a y-direction. As shown in the figure, the example biosensor device includes an active device region 104. In some embodiments, the active device region 104 comprises a transistor device area including source, drain, channel, and body regions of a transistor. The active device region 104 may be referred to as an oxide definition (OD) region. The source, drain, and body regions of the active device region 104 are depicted in FIG. 1A via the "D," "S," and "B" notations, respectively. The channel region (not labeled in FIG. 1A) is formed in the active device region 104 between the source and drain regions. In some embodiments, the active device region 104 is formed in a top silicon layer of a silicon-on-insulator (SOI) wafer.

The example biosensor device of FIG. 1A further includes a gate 106 that is formed under the active device region 104. In some embodiments, the gate 106 is the gate of the transistor formed in the active device region 104 and comprises polysilicon, a metal, a metal alloy, or another material. A cavity 102 (e.g., a trench, an opening, a well, etc.) is formed over a portion of the gate 106. In the example biosensor device of FIG. 1A, the cavity 102 functions as a sensing area or sensing volume (e.g., a sensing region) that is configured to receive a molecule (e.g., a charged molecule, a biomolecule, etc.) or other entity (e.g., a bio-entity, etc.). In embodiments, the cavity 102 includes a sensing surface with a bio- or biochemical-compatible layer or a biofunctionalized layer of immobilized probe molecules that act as surface receptors. A great variety of biomolecules and bio-entities may be used to functionalize the sensing surface of the cavity 102 (e.g., ions, enzymes, antibodies, ligands, receptors, peptides, oligonucleotides, cells of organs, organisms, pieces of tissue, etc.). For instance, to detect ssDNA (single-stranded deoxyribonucleic acid), the cavity 102 may be functionalized with immobilized complementary ssDNA strands. Also, to detect various proteins such as tumor markers, the sensing surface may be functionalized with monoclonal antibodies.

A binding of target molecules or entities to the sensing surface of the cavity 102 causes the biosensor device to generate an output (e.g., an electrical signal, a voltage, a current, etc.) indicative of the binding event. In embodiments described herein, the binding of charged molecules (e.g., charged biomolecules) to the sensing surface of the cavity 102 causes the biosensor device to generate an output indicative of a number of charged molecules present in the cavity 102 (e.g., a number of charged molecules immobilized on a bottom surface of the cavity 102), a molecule density in the cavity 102 (e.g., a number of charged molecules per unit area on the bottom surface of the cavity), and/or a charge density in the cavity 102 (e.g., amount of charge per unit area on the bottom surface of the cavity). In some examples, the biosensor device operates in a dry environment, such that the cavity 102 is configured to immobilize charged molecules without a fluidic solution. In other examples, the biosensor device operates in a wet environment, with the cavity 102 holding a fluidic solution including charged molecules. A bottom surface of the cavity 102 is configured to immobilize at least some of the charged molecules of the solution, in embodiments. Further, in examples, the biosensor device is configured to generate an output indicative of a pH of a fluidic solution in the cavity 102. Such examples are described in further detail herein.

Figure 1B:
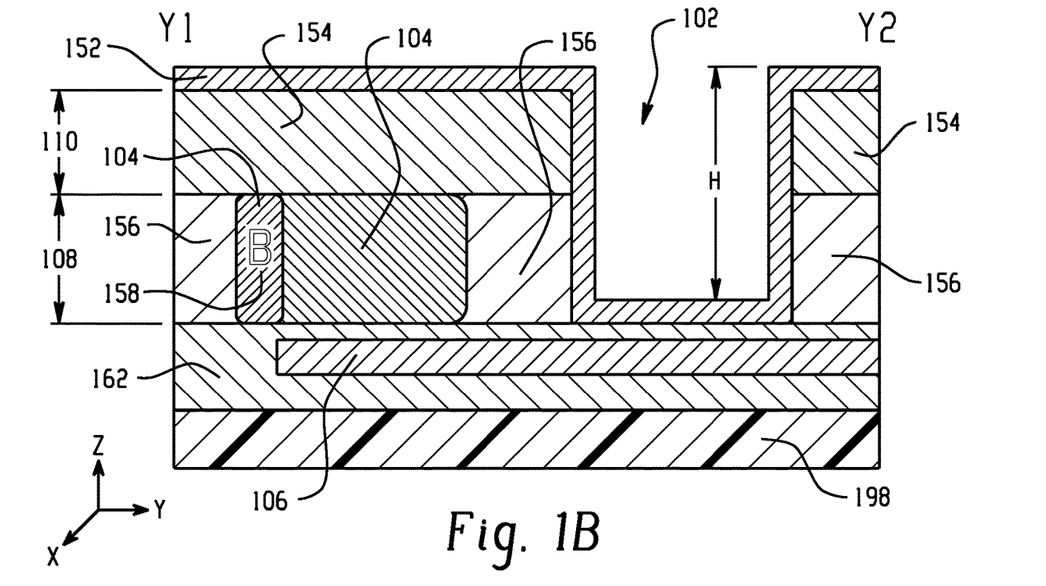
Figure 1C:
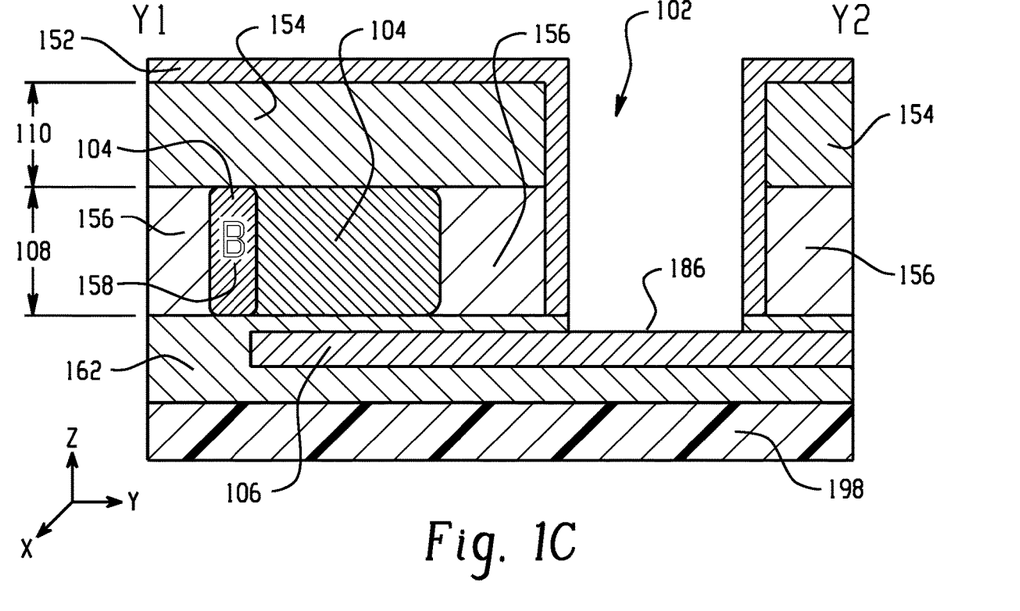
Figure 1D:
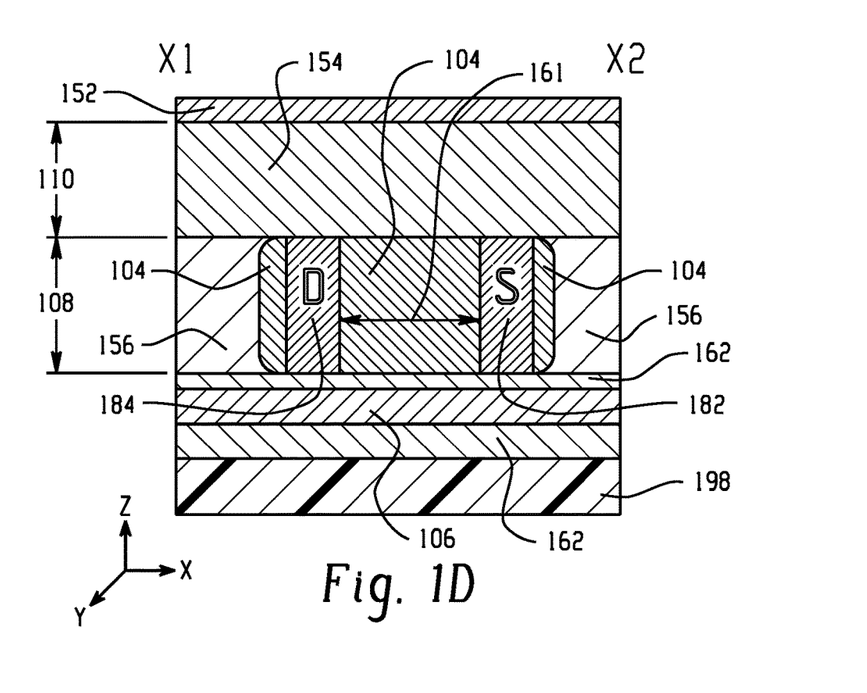

To further illustrate the biosensor device of FIG. 1A, reference is made to FIG. 1B, which depicts a cross-sectional view of the device along the Y1-Y2 cutline. As shown in FIG. 1B, in embodiments, the device includes a shallow trench isolation (STI)/active device region layer 108 and a dielectric layer 110 formed over the STI/active device region layer 108. The STI/active device region layer 108 comprises the above-described active device region 104 (or a portion thereof), which includes a body region 158 of the transistor formed in the active device region 104. The active device region 104 formed in the STI/active device region layer 108 further includes the source, drain, and channel regions of the transistor formed in the active device region 104. Such source, drain, and channel regions are not visible in the cross-sectional view of FIG. 1B but are depicted in FIG. 1D at reference numerals 182, 184, 161, respectively.

The active device region 104 of the STI/active device region layer 108 is surrounded by shallow trench isolation (STI) insulator material 156, as shown in FIG. 1B. The dielectric layer 110 formed over the STI/active device region layer 108 comprises a dielectric material 154 (e.g., silicon oxide, silicon dioxide, another type of oxide, a nitride, etc.). In examples, the dielectric layer 110 is a buried oxide layer of a silicon-on-insulator (SOI) wafer, and the active device region 104 of the layer 108 is formed in a top silicon layer of the SOI wafer. The fabrication of the biosensor devices described herein using SOI wafers is described in further detail below with reference to FIGS. 7A-7D. It is noted that in other embodiments, SOI wafers are not used in fabricating the biosensor devices described herein. In such other embodiments, different types of substrates (e.g., a substrate comprising a semiconductor material, such as a silicon substrate, etc.) are used in fabricating the biosensor devices described herein.

Also depicted in FIG. 1B are the cavity 102 and the gate 106. The cavity 102 has a height H in the z-direction that is within an approximate range of 0.1 µm-10 µm, in examples. As shown in the figure, the cavity 102 is disposed above a portion of the gate 106 and comprises an opening that is formed in the STI/active device region layer 108 and the dielectric layer 110. The gate 106 is formed in a dielectric layer 162 that comprises a dielectric material (e.g., inter-layer dielectric (ILD) material), in examples. As illustrated in the figure, the dielectric material of the dielectric layer 162 is disposed between the gate 106 and the STI/active device region layer 108. The structure is formed on a substrate 198. In embodiments, the substrate 198 is a "handling wafer." As described in greater detail below, in embodiments, the biosensor device is fabricated using a SOI wafer. To fabricate the biosensor device using the SOI wafer, a top silicon layer of the SOI wafer is attached to a handling wafer, such as the substrate 198 shown in FIG. 1B. Subsequently, processing of a backside of the SOI wafer (e.g., removing the bottom silicon substrate, performing backside etching through the dielectric layer 110, etc.) is performed. The use of the handling wafer and the fabrication of the device using the SOI wafer is described in greater detail below.

In embodiments, the biosensor device includes an insulating layer 152, as shown in FIG. 1B. The insulating layer 152 comprises $HFO_2$, $SrTiO_3$, $ZrO_2$, $HfSiO_4$, $La_2O_3$ and $TiO_2$, or another dielectric material, in examples. In embodiments, the insulating material 152 comprises a dielectric material having a relatively high dielectric constant, e.g., a dielectric constant within an approximate range of 10-100. In the example of FIG. 1B, the insulating layer 152 covers sidewalls and a bottom surface of the cavity 102. In this example, portions of the insulating layer 152 in the cavity 102 may comprise a sensing surface with a bio- or bio-chemical-compatible layer that acts as a surface receptor configured to immobilize molecules (e.g., charged molecules). In particular, the portion of the insulating layer 152 formed over the bottom surface of the cavity 102 may be configured to immobilize charged molecules, such that the immobilized molecules are in relatively close proximity to the portion of the gate 106 formed under the cavity 102.

Figure 1E:
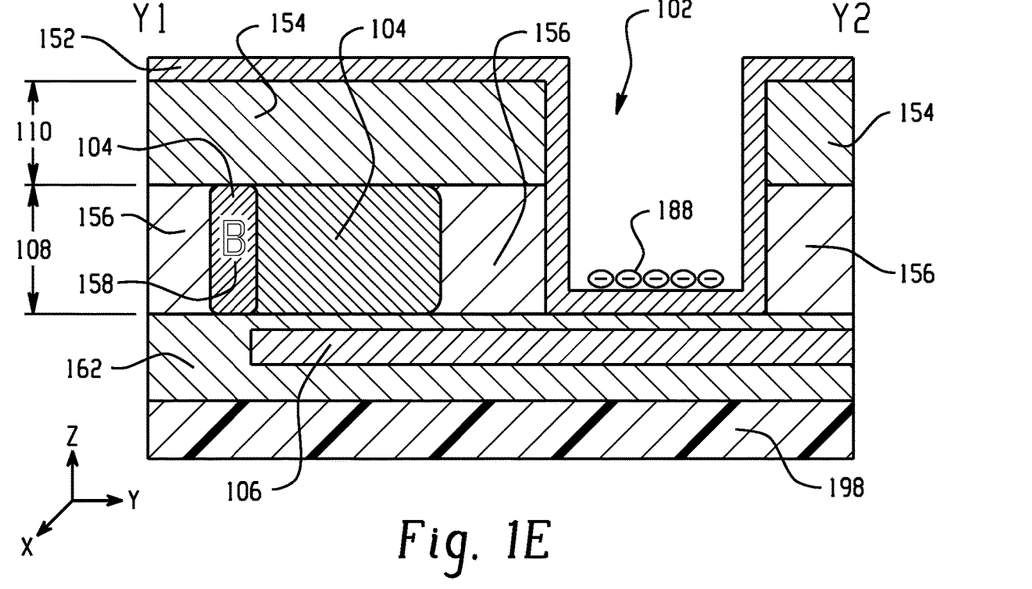

As described in further detail below with reference to FIGS. 1E and 1F, the immobilization of charged molecules in the cavity 102 (e.g., directly on the gate 106 or in a vicinity of the gate 106) causes a voltage potential of the gate 106 to change, thus enabling the biosensor device to generate an output indicative of a number of charged molecules present in the cavity 102 (e.g., a number of charged molecules immobilized on the bottom surface of the cavity 102), a molecule density in the cavity 102 (e.g., a number of charged molecules per unit area on the bottom surface of the cavity 102), and/or a charge density in the cavity 102 (e.g., amount of charge per unit area on the bottom surface of the cavity 102).

As described above, in the example of FIG. 1B, the insulating layer 152 covers the sidewalls and the bottom surface of the cavity 102. By contrast, in other examples, the insulating layer 152 is not formed over the bottom surface of the cavity 102. An example of this is shown in FIG. 1C, which depicts the insulating layer 152 formed on the sidewalls of the cavity 102 but not formed on a bottom surface 186 of the cavity 102. As illustrated in this figure, the bottom surface of the cavity 102 comprises a portion 186 of the gate 106. Thus, in the embodiment of FIG. 1C, the portion 186 of the gate 106 is configured to immobilize molecules (e.g., charged molecules) directly on the gate 106 (e.g., with or without the use of surface receptors or another material for immobilizing the molecules).

To further illustrate the biosensor device of FIGS. 1A-1C, reference is made to FIG. 1D, which depicts a cross-sectional view of the device along the X1-X2 cutline. From this view, it can be seen that the active device region 104 of the STI/active device region layer 108 includes source and drain regions 182, 184 of the transistor formed in the active device region 104. The active device region 104 further includes a channel region 161 that connects the source and drain regions 182, 184, and the active device region 104 is surrounded by STI insulator material 156. Also depicted in FIG. 1D are the above-described insulating layer 152, dielectric layer 110, gate 106, dielectric layer 162, and substrate 198.

The operation of the biosensor device of FIGS. 1A-1D is described with reference to FIGS. 1E and 1F. In FIG. 1E, a bottom surface of the cavity 102 is configured to immobilize charged molecules 188 in relative close proximity to the portion of the gate 106 disposed below the cavity 102. The charges of the charged molecules 188 cause a charge density on the gate 106 to change, which results in a change in the voltage potential of the gate 106. The voltage potential of the gate 106 thus varies based on the charged molecules 188 immobilized in the cavity 102 (e.g., a number of the molecules 188 and/or a charge density on the gate 106 resulting from the molecules 188, etc.). As described above, the gate 106 is the gate for the transistor formed in the active device region 104, such that a current between the source and drain regions 182, 184 (e.g., which may be referred to as a "drain current") of the transistor varies based on the voltage potential of the gate 106.

Figure 6A:
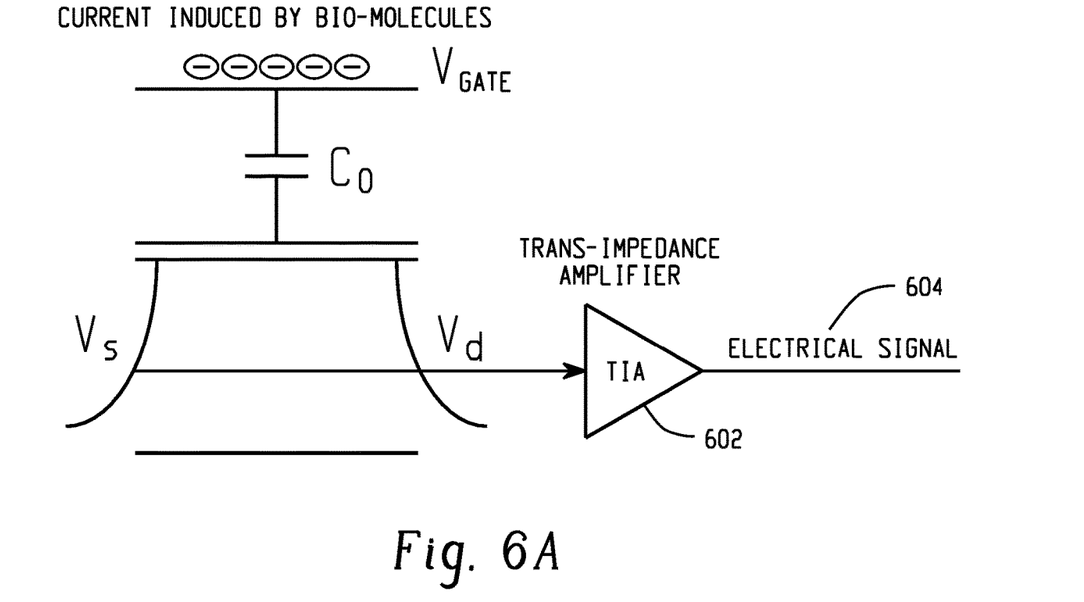
FIGS. 6A and 6B depict trans-impedance amplifiers used in generating an output signal, in accordance with some embodiments.
Figure 6B:
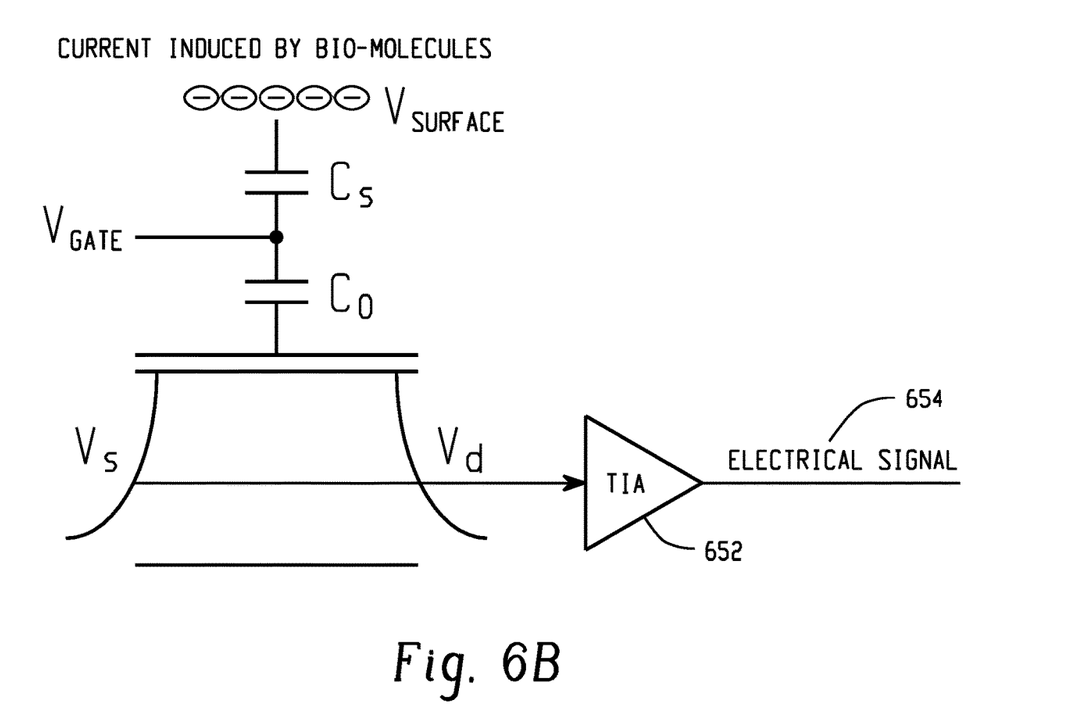

In examples, the current between the source and drain regions 182, 184 is measured, and the measured current (or a change in the measured current caused by the immobilization of the charged molecules 188) is indicative of a number of the charged molecules 188, a molecule density of the molecules 188, and/or a charge density at the bottom surface of the cavity 102 caused by the molecules 188. Thus, in such examples, the detection mechanism is a conductance modulation of the transducer due to the binding of the charged molecules 188 in the cavity 102. In other examples, one or more components (e.g., a trans-impedance amplifier, as depicted in FIGS. 6A and 6B) are used to translate the current or change of current induced by the charged molecules 188 into another electrical signal, such as a measurable voltage.

The source and drain regions 182, 184 comprise areas of P-type doping formed in a lightly-doped N-well, in embodiments. The P-type doping is achieved via an ion implantation procedure, in some examples. The use of the P-type doping may allow a maximum drain current $I_D$ induced by the immobilization of the charged molecules 188 to be obtained. Accordingly, with the maximum drain current $I_D$, the transconductance $g_m$ of the MOSFET transistor is likewise maximized. In other examples, the source and drain regions 182, 184 comprise areas of N-type doping.

Figure 1F:
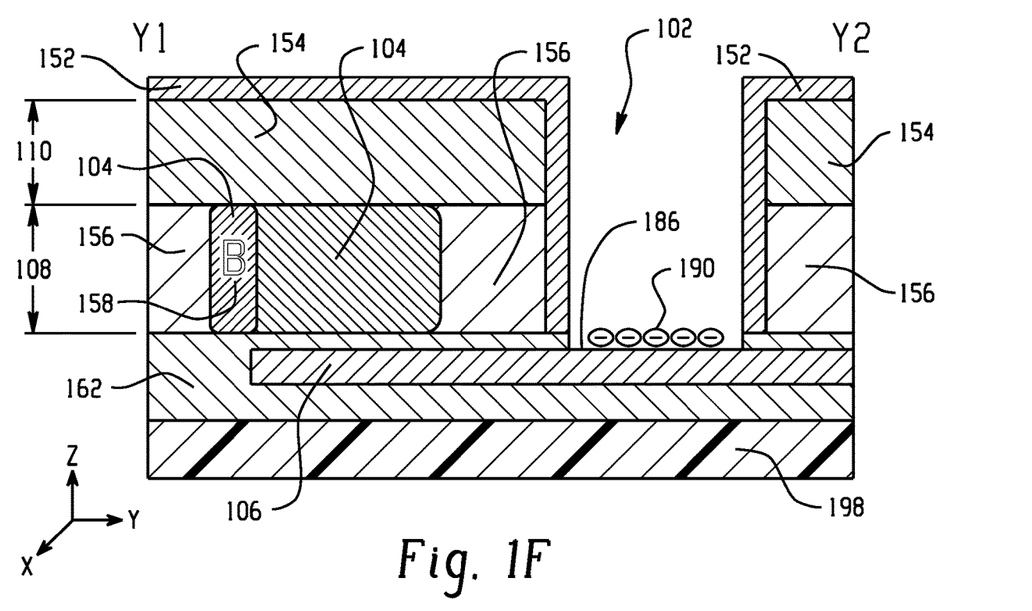

In the example of FIG. 1F, the insulating layer 152 is not formed over a bottom surface of the cavity 102, such that the gate 106 is configured to immobilize charged molecules 190 directly on the gate 106 (e.g., with or without the use of surface receptors or another material for immobilizing the molecules on the surface 186). The charges of the charged molecules 190 cause a charge density on the gate 106 to change, which results in a change in the voltage potential of the gate 106. The voltage potential of the gate 106 thus varies based on the charged molecules 190 immobilized in the cavity 102. Because the gate 106 functions as a gate for the transistor formed in the active device region 104, a current between the source and drain regions 182, 184 of the transistor likewise varies based on the binding of the charged molecules 190. This current (or another electrical signal based on the current) is indicative of a number of the charged molecules 190, a molecule density of the molecules 190, and/or a charge density at the bottom surface of the cavity 102 caused by the molecules 190.

The above-described biosensor device includes, among other components, (i) the cavity 102, (ii) the transistor formed in the active device region 104 including the channel, source, and drain regions 161, 182, 184, and (iii) the gate 106. From FIGS. 1A-1D, it can be seen that the channel, source, and drain regions 161, 182, 184 of the transistor are spatially separated from the cavity 102 in a lateral direction (i.e., the x-direction, the y-direction, or both the x- and y-directions). For instance, in the example of FIGS. 1A-1D, the source, drain, and channel regions of the transistor are spatially separated from the cavity 102 in the y-direction. The gate 106 extends between the cavity 102 and the channel, source, and drain regions 161, 182, 184 and couples together these spatially-separated components in the manner described above (e.g., the binding of charged molecules in the cavity 102 results in a change in the voltage potential of the gate 106, which in turn results in a change in the current between the source and drain regions 182, 184).

The biosensors of the instant application differ from conventional biosensors. Typically, in conventional biosensors, a sensing region (e.g., a cavity) is formed directly above a transistor. Any spatial separation between the sensing region and the source, drain, and channel regions of the transistor is in a vertical direction (i.e., the z-direction) and not in a lateral direction. Further, in such conventional biosensors, because the sensing region is formed directly above the transistor, a size of the sensing region is limited by a size of the transistor. Consequently, to increase the size of the sensing region, the size of the transistor must be increased accordingly. This is generally undesirable because increasing the size of the transistor increases an amount of noise in the biosensing operation. Thus, in the conventional biosensors, any increase in signal provided by an enlarged sensing region is accompanied by an increase in noise, such that a sensitivity (e.g., a signal-to-noise ratio (SNR)) of the biosensor is not increased by enlarging the sensing region. Further, in the conventional biosensors, if the transistor size is not enlarged, the sensing region may be relatively small, such that biosensing cannot be performed for molecules of relatively large sizes.

In contrast to these conventional biosensors, the biosensors of the instant application utilize a sensing region (e.g., the cavity 102) that is not formed directly above a transistor. Rather, as described above, the sensing region is spatially separated from the transistor in a lateral direction. Because of this lateral separation and because the sensing region is not formed directly over the transistor, a size of the sensing region (e.g., a size of the cavity 102) is not dependent on a size of the transistor. Accordingly, a size of the sensing region can be increased without having to increase the transistor size, thus enabling an increased sensing signal without an accompanying increase in noise. In examples, the SNR and sensitivity of the biosensors of the instant application are higher than those of the conventional biosensors. For instance, a conventional biosensor having a sensing region with an area of 1 $\mu m^2$ has an SNR of approximately 1.6, in an embodiment. By contrast, an example biosensor of the instant application having a sensing region with an area of 10 $\mu m^2$ (i.e., an area that is 10 times larger than the area of the conventional biosensor) has an SNR of approximately 16 (i.e., an SNR that is 10 times larger than the SNR of the conventional biosensor), in an embodiment. Further, because a size of the sensing region can be increased without having to increase the transistor size, the sensing region can be made relatively large in size, thus enabling biosensing to be performed for molecules of relatively large sizes. The biosensors of the instant disclosure enable biosensing of DNA molecules and protein molecules, among others.

Figure 2:
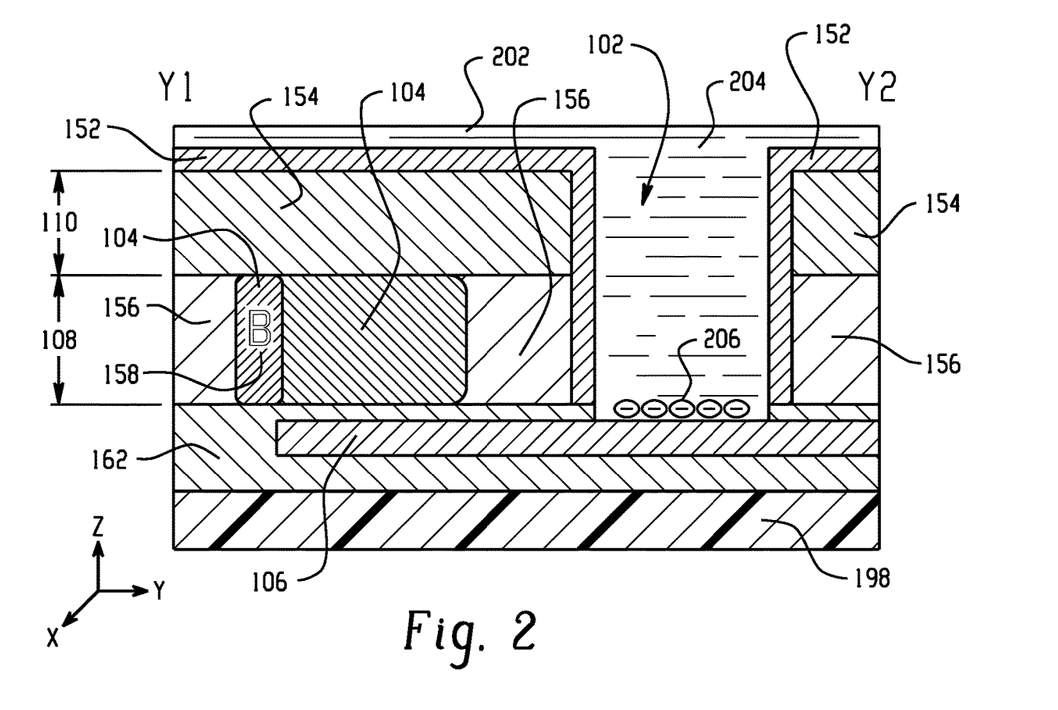
FIG. 2 depicts aspects of an example biosensing operation performed in a wet environment, in accordance with some embodiments.

FIG. 2 depicts aspects of an example biosensing operation performed in a wet environment, in accordance with some embodiments. In the example of FIG. 2, the cavity 102 holds a fluidic solution 202 including charged molecules 206. A bottom surface of the cavity 102 is configured to immobilize at least some of the charged molecules, as illustrated in the figure. In order to give the fluidic solution 202 a voltage potential, a reference electrode 204 is utilized. The biosensing operation is performed in a manner similar to that described above, with a voltage potential of the gate 106 being based on the charged molecules 206 present in the cavity 102, and a current between source and drain regions 182, 184 of the transistor being based on the voltage potential of the gate 106. In examples, this current is measured, and the measured current is indicative of a number of the charged molecules 206, a molecule density of the molecules 206 immobilized in the cavity 102, and/or a charge density on the bottom surface of the cavity 102. In other examples, the current is translated into another measurable electrical signal (e.g., a voltage). The translation of a current into another measurable electrical signal is described below with reference to FIGS. 6A and 6B.

The biosensor devices described herein may also be used to generate an output indicative of a pH of the fluidic solution 202 present in the cavity 102. In examples where the biosensor device is used as a pH sensor, the fluidic solution 202 may or may not include charged molecules 206. In such examples, a voltage potential of the gate 106 is based on the pH of the fluidic solution 202 present in the cavity 102, and a current between source and drain regions 182, 184 of the transistor is based on the voltage potential of the gate 106. In examples, this current is measured, and the measured current is indicative of the pH of the fluidic solution 202. In other examples, the current is translated into another measurable electrical signal.

Figure 3:
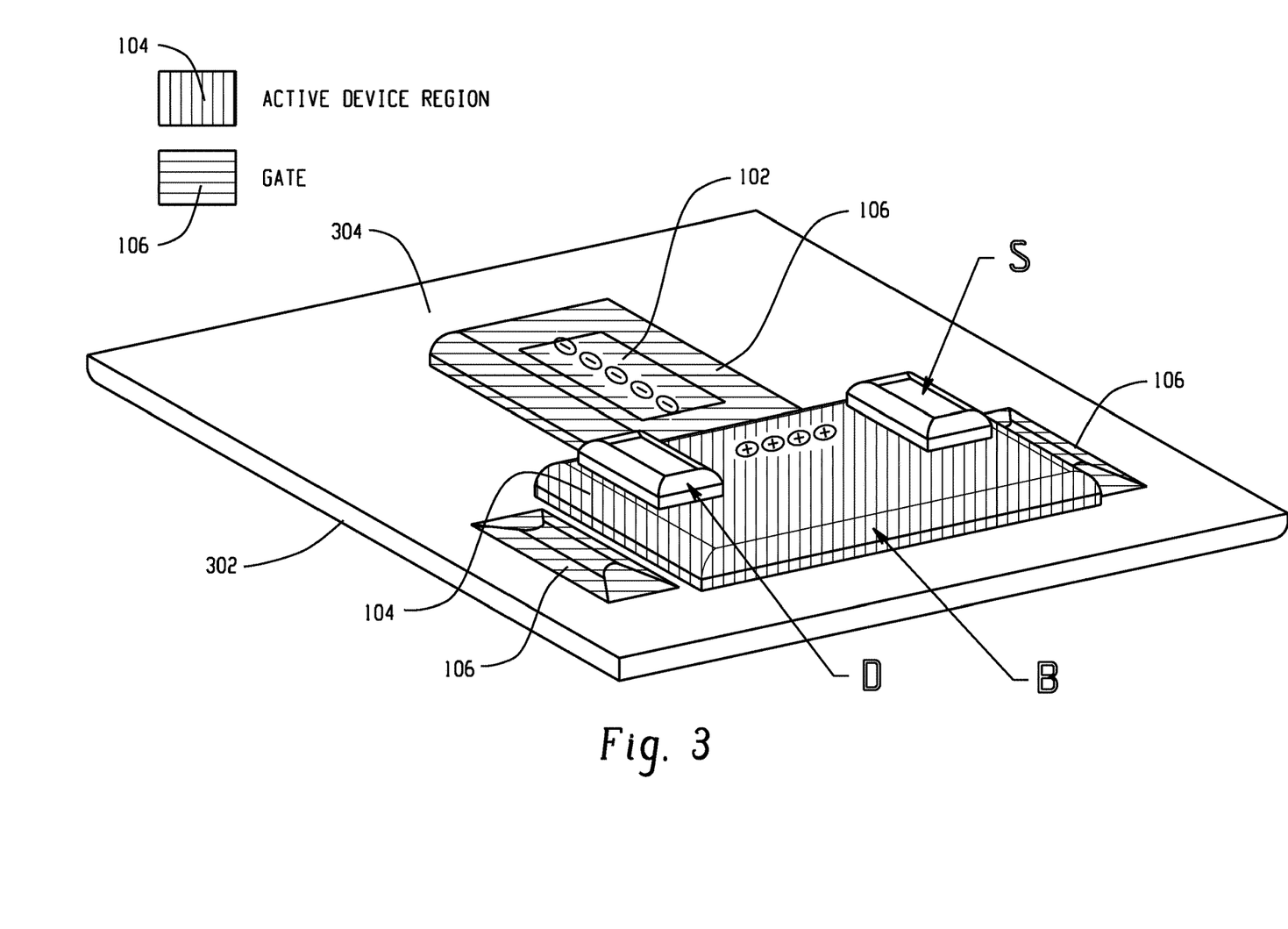
FIG. 3 is a three-dimensional depiction of an example biosensor device, in accordance with some embodiments.

FIG. 3 is a three-dimensional depiction of an example biosensor device, in accordance with some embodiments. This figure depicts the above-described cavity 102, active device region 104, and gate 106. In embodiments, the active device region 104 comprises a transistor device area including source, drain, channel, and body regions of a transistor. The active device region 104 is electrically isolated from other regions (e.g., other active device regions) by STI insulator material 304 that is formed above the gate 106. The structure is formed on a substrate 302 (e.g., a silicon substrate, a glass substrate, etc.). In embodiments, the substrate 302 is a handling wafer. The use of a handling wafer in the fabrication of the biosensor device is described in greater detail below with reference to FIGS. 7A-7D.

As described above with reference to FIGS. 1A-2, in the biosensor devices of the instant application, a voltage potential of the gate 106 varies based on charged molecules that are immobilized in a cavity, with the immobilized molecules being located in relative close proximity to a portion of the gate 106 or in direct contact with the gate 106. The charged molecules induce a charge on the gate 106, which causes the voltage potential of the gate 106 to change. In embodiments, a charge density of the immobilized charged molecules is $$Q_d = \frac{Q}{A}, \qquad \text{(Equation 1)}$$

where $Q_d$ is a charge density in coulombs per meter squared (i.e., $C/m^2$), Q is the total amount of charge in coulombs of the immobilized charged molecules, and A is the area over which the charged molecules are immobilized. As an example, for 20 BP DNA strand, 1 DNA molecule in 1 $\mu m^2$ area yields a charge density of $Q_d=3.2\times10^{-7}$ $C/m^2$. The voltage potential of the gate 106 is based on the charge density $Q_d$ at the site of immobilization. As described above, in some examples, a portion of the gate is configured to immobilize the charged molecules, and in other examples, the insulating layer 152 formed over a bottom surface of the cavity 102 is configured to immobilize the charged molecules.

Figure 4A:
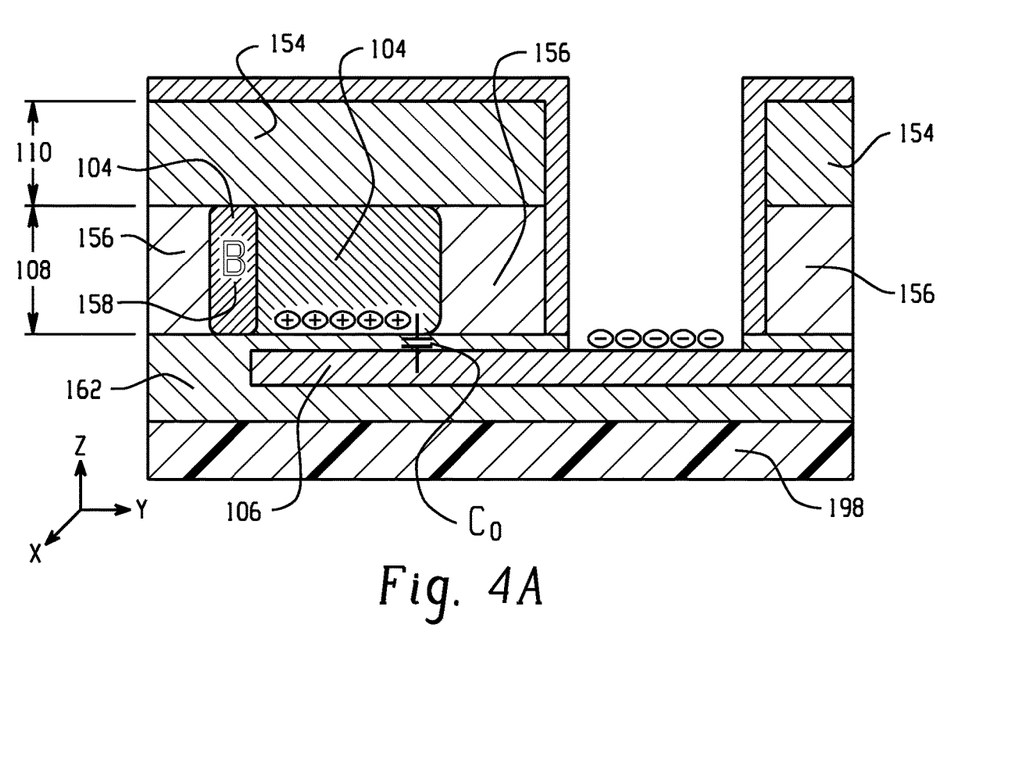
FIGS. 4A and 4B depict an example biosensor device and corresponding equivalent circuit, in accordance with some embodiments.
Figure 4B:
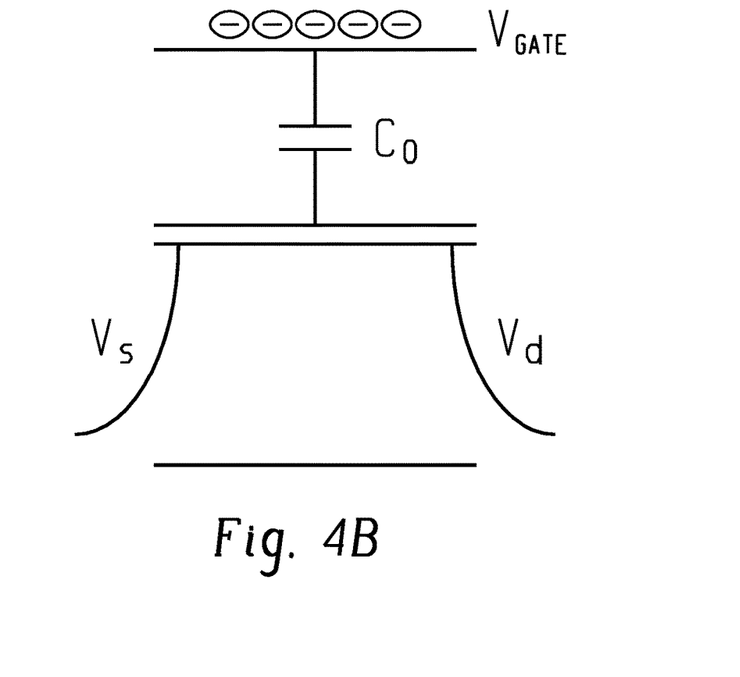

In examples, the voltage potential of the gate 106 is also based on one or more parasitic elements (e.g., one or more parasitic capacitances) of the biosensor device. To illustrate this, reference is made to FIGS. 4A and 4B. FIG. 4A depicts the example biosensor device of FIG. 1C, which permits immobilization of charged molecules directly on the gate 106. As shown in FIG. 4A, a parasitic capacitance "$C_0$" exists between the gate 106 and the active semiconductor region 104 of the STI/active device region layer 108. In examples, the parasitic capacitance $C_0$ exists specifically between the gate 106 and the channel region 161 that connects source and drain regions 182, 184 (e.g., as depicted in FIG. 1D) of the transistor formed in the active device region 104. FIG. 4B depicts an equivalent circuit that corresponds to the biosensor device of FIG. 4A, with the equivalent circuit including the parasitic capacitance $C_0$.

The voltage potential of the gate 106 for the example of FIGS. 4A and 4B is given by the following:

$$V_{gate} = \frac{Q}{C_0} = \frac{Q_d A}{\epsilon_r \epsilon_0 \frac{A}{d}} = \frac{Q_d d}{\epsilon_r \epsilon_0}, \qquad \text{(Equation 2)}$$

where $V_{gate}$ is the voltage potential of the gate 106, Q is the total amount of charge in coulombs of the molecules immobilized in the cavity, $C_0$ is the above-described parasitic capacitance, A is the area over which the charged molecules are immobilized, d is a thickness (e.g., several nanometers, tens of nanometers, etc.) of a portion of the dielectric layer 162 formed between the gate 106 and the active device region 104, $\epsilon_r$ is a permittivity of the dielectric layer 162, and $\epsilon_0$ is the dielectric constant of air. From Equation 2, it can be seen that the voltage potential of the gate 106 depends on both the charge density $Q_d$ and the parasitic capacitance $C_0$, among other variables.

Figure 5A:
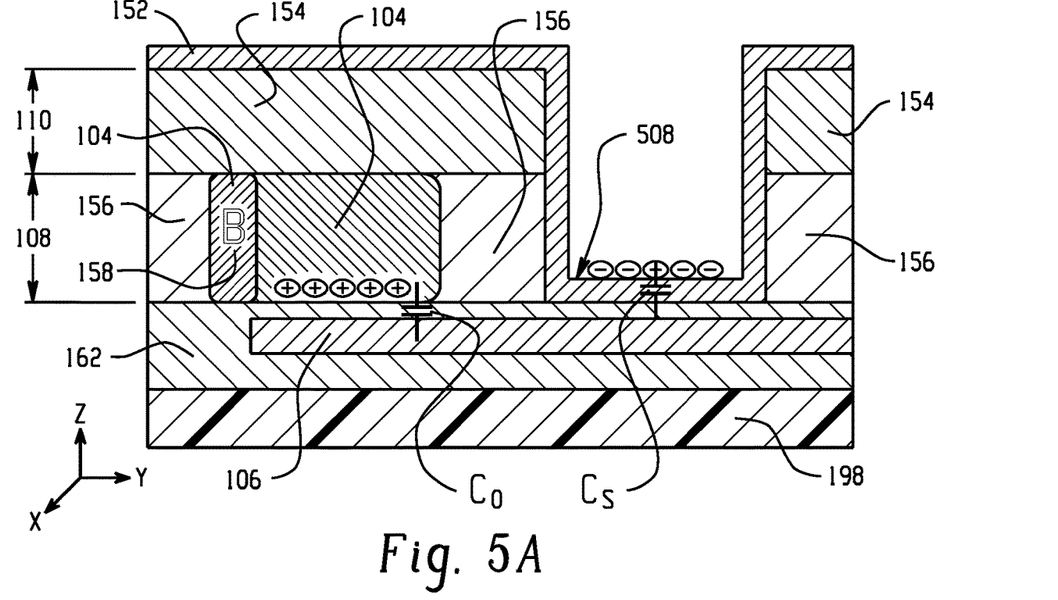
FIGS. 5A and 5B depict another example biosensor device and corresponding equivalent circuit, in accordance with some embodiments.
Figure 5B:
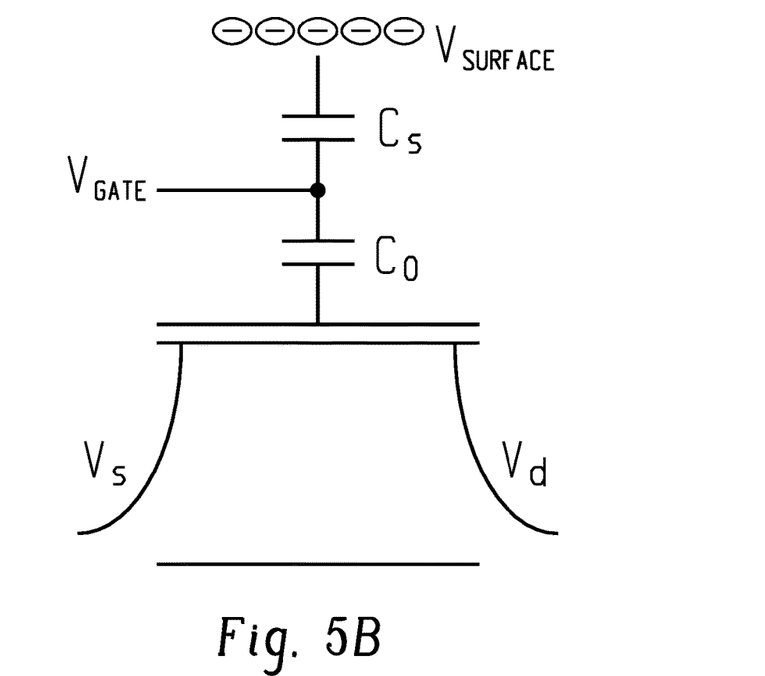

To further illustrate the effect of parasitic elements on the voltage potential of the gate 106, reference is made to FIGS. 5A and 5B. FIG. 5A depicts the example biosensor device of FIG. 1B, which includes the insulating layer 152 formed on a bottom surface of the cavity. The insulating layer 152 is configured to immobilize charged molecules, as depicted in FIG. 5A. As shown in this figure, a parasitic capacitance Cs exists between the gate 106 and a surface 508 of the insulating layer 152 on which the charged molecules are immobilized. Additionally, the parasitic capacitance $C_0$ (described above with reference to FIGS. 4A and 4B) is present. FIG. 5B depicts an equivalent circuit that corresponds to the biosensor device of FIG. 5A, with the equivalent circuit including the parasitic capacitances Cs and $C_0$.

The voltage at the surface 508 is given by the following:

$$V_{surface} = \frac{Q}{\frac{CsC_0}{Cs+C_0}} = \frac{Q_d d(1+a)}{a \epsilon_r \epsilon_0}, \qquad \text{(Equation 3)}$$

where $Cs=aC_0$. The voltage potential of the gate 106 for the example of FIGS. 5A and 5B is given by the following:

$$V_{gate} = \frac{a}{1+a} V_{surface}. \qquad \text{(Equation 4)}$$

From Equations 3 and 4, it can be seen that the voltage potential of the gate 106 depends on both the charge density $Q_d$ and the parasitic capacitances Cs and $C_0$.

In examples where the sensor cavity (e.g., the cavity 102) is relatively small in size (e.g., an area of the bottom surface of the sensor cavity is relatively small), Cs is much smaller than $C_0$, and the following is true:

if Cs<<$C_0$, then a<<1, and $V_{gate}=aV_{surface}$

Conversely, in examples where the sensor cavity is relatively large in size (e.g., an area of the bottom surface of the sensor cavity is relatively large), Cs is much larger than $C_0$, and the following is true:

if Cs>>$C_0$, then a>>1, and $V_{gate} \sim V_{surface}$

In order to enlarge the SNR of the biosensor device, Cs should be much larger than $C_0$, and this is achieved by enlarging the size of the sensor cavity. As described above, under the approaches of the instant application, the size of the sensor cavity can be enlarged without an accompanying increase in the size of the transistor. This is because the cavity is spatially separated from the transistor in a lateral direction, such that the cavity is not formed over the transistor. Accordingly, the size of the cavity can be enlarged to achieve a higher sensing signal without the increase in noise that would present if the transistor size was enlarged.

As described above, in some examples, a current between source and drain regions 182, 184 (e.g., also referred to as the "drain current" ($I_D$)) is measured (e.g., sensed), with the measured current being the output of the biosensor device. In other examples, this current is not measured, and instead, one or more components are used to translate the current into a different electrical signal that can be measured. To illustrate this, reference is made to FIGS. 6A and 6B, which depict trans-impedance amplifiers 602, 652 used in generating electrical signals 604, 654, respectively, in accordance with some embodiments. FIG. 6A depicts the equivalent circuit of FIG. 4B and shows that a drain current induced by the immobilization of the biomolecules on the gate 106 is translated into the electrical signal 604 by the trans-impedance amplifier 602. Likewise, FIG. 6B depicts the equivalent circuit of FIG. 5B and shows that a drain current induced by the immobilization of the biomolecules on the surface of the insulating layer 152 is translated into the electrical signal 654 by the trans-impedance amplifier 652. The electrical signals 604, 654 may be, for example, voltages (e.g., voltage signals) that can be measured.

In embodiments, other components are included as parts of the biosensor devices described herein. For example, in embodiments, an on-chip heater is integrated with the biosensing transistor. In other embodiments, a thermal sensor is integrated with the biosensing transistor. The type of temperature sensor can be thermal-resistive, diode-based, or CMOS-based. In embodiments, various sensing circuits are integrated with the biosensing transistor.

As described above, in examples, the biosensor devices of the instant application are fabricated using SOI wafers. In one example fabrication process, an SOI wafer is bonded to a handling wafer. The SOI wafer is bonded to the handling wafer at the top silicon layer (e.g., the thinner silicon layer) of the SOI wafer, such that the bottom silicon layer (e.g., the thicker silicon layer) of the SOI wafer remains exposed. Subsequently, the bottom silicon layer is removed, thus exposing the buried oxide layer of the SOI wafer. After removing the bottom silicon layer, the cavity (e.g., the cavity 102) is etched into the buried oxide layer using a backside etching process.

Figure 7A:
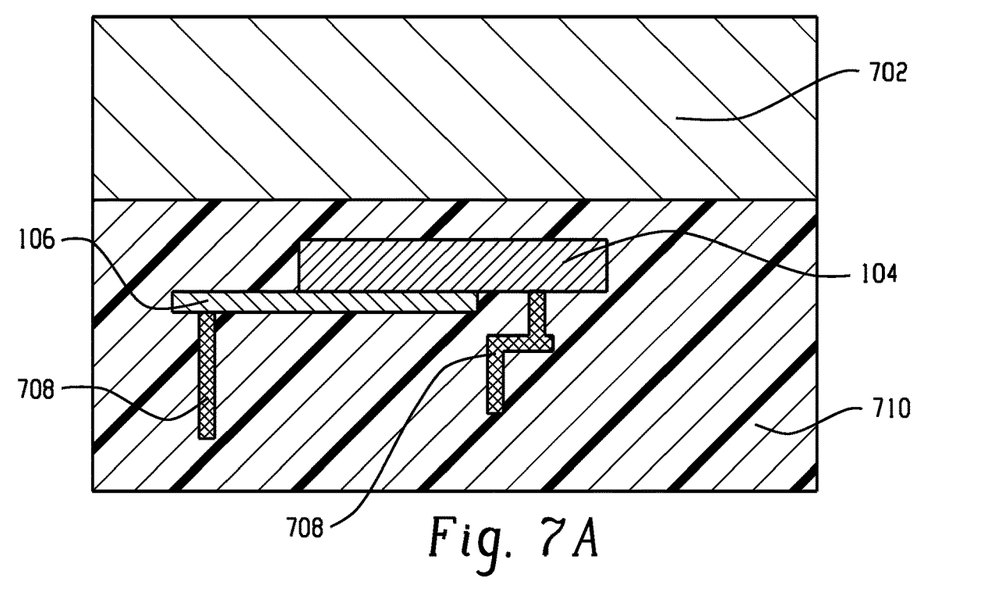
FIGS. 7A-7D depict example steps used in fabricating a biosensor device, in accordance with some embodiments.

To illustrate an example process for fabricating the biosensor devices of the instant application, reference is made to FIGS. 7A-7D. FIG. 7A depicts the active device region 104 and the gate 106, described above. Inter-layer dielectric (ILD) insulator material 710 surrounds the active device region 104, and metals for interconnections 708 are coupled to the active device region 104 and the gate 106. A substrate 702 (e.g., a silicon substrate) is shown as being above the features 104, 106, 708, 710, such that the structure is turned upside-down in the step shown in FIG. 7A. In embodiments, the substrate 702 is the bottom silicon layer of an SOI wafer, and the active device region 104 is formed in the top silicon layer of the SOI wafer. In such embodiments, an oxide layer (e.g., a "buried oxide" or "Box" layer) of the SOI wafer is disposed between the substrate 702 and the active device region 104.

Figure 7B:
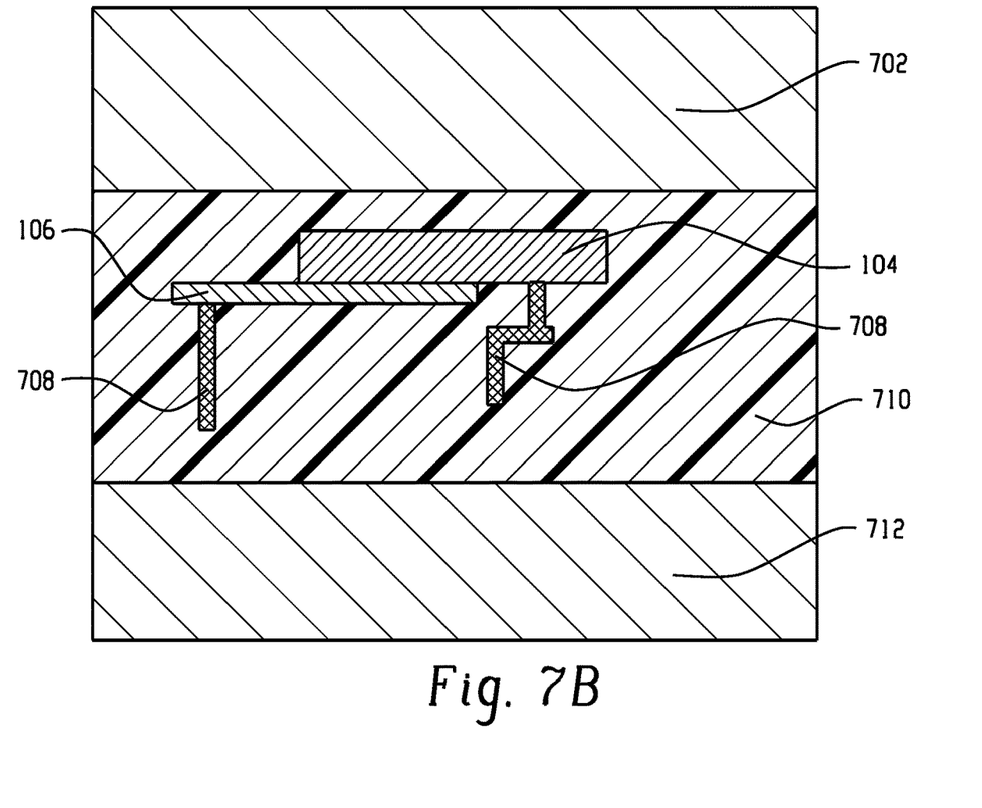

After forming the features shown in FIG. 7A, in the step shown in FIG. 7B, the structure is bonded to a handling substrate 712. In the subsequent step shown in FIG. 7C, the substrate 702 is removed. In examples, the removal of the substrate 702 is performed using one or more of mechanical grinding, chemical mechanical polishing (CMP), wet etching, and dry etching. Next, in the step shown in FIG. 7D, the structure is etched as shown to form the cavity 102, which is described above. In some embodiments where the structure is formed using the SOI wafer, the etching of the structure includes the etching of the buried oxide layer of the SOI wafer.

Figure 7C:
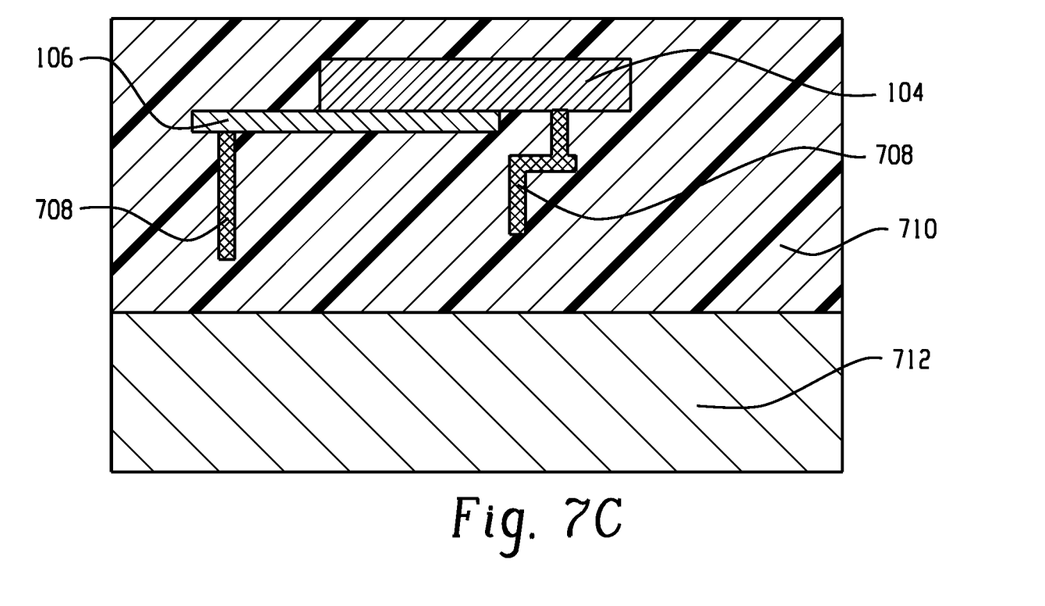
Figure 7D:
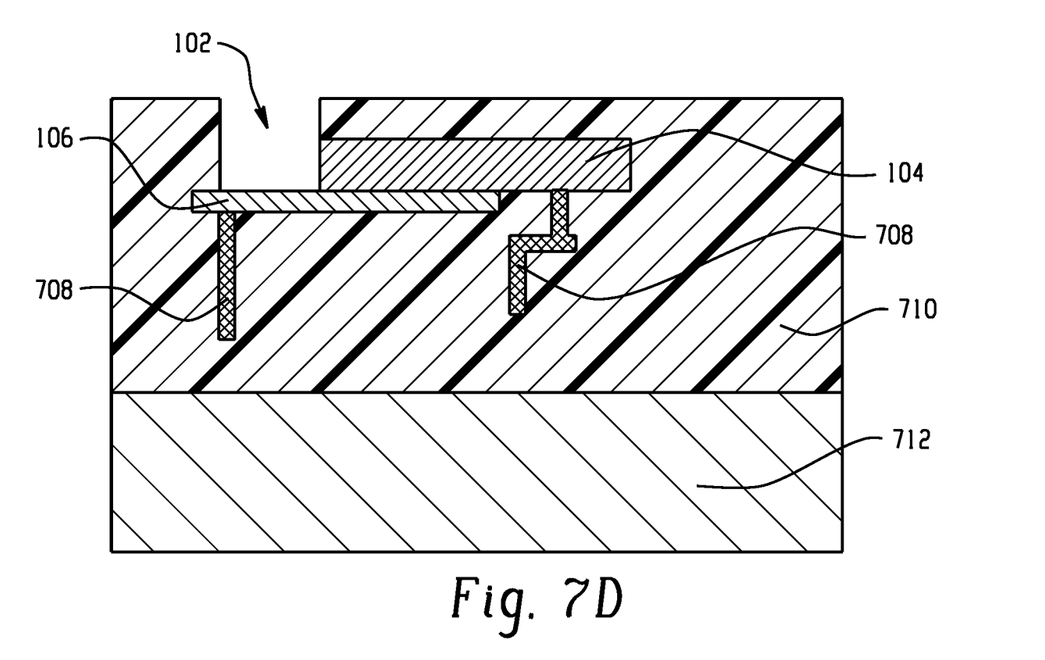
Figure 8:
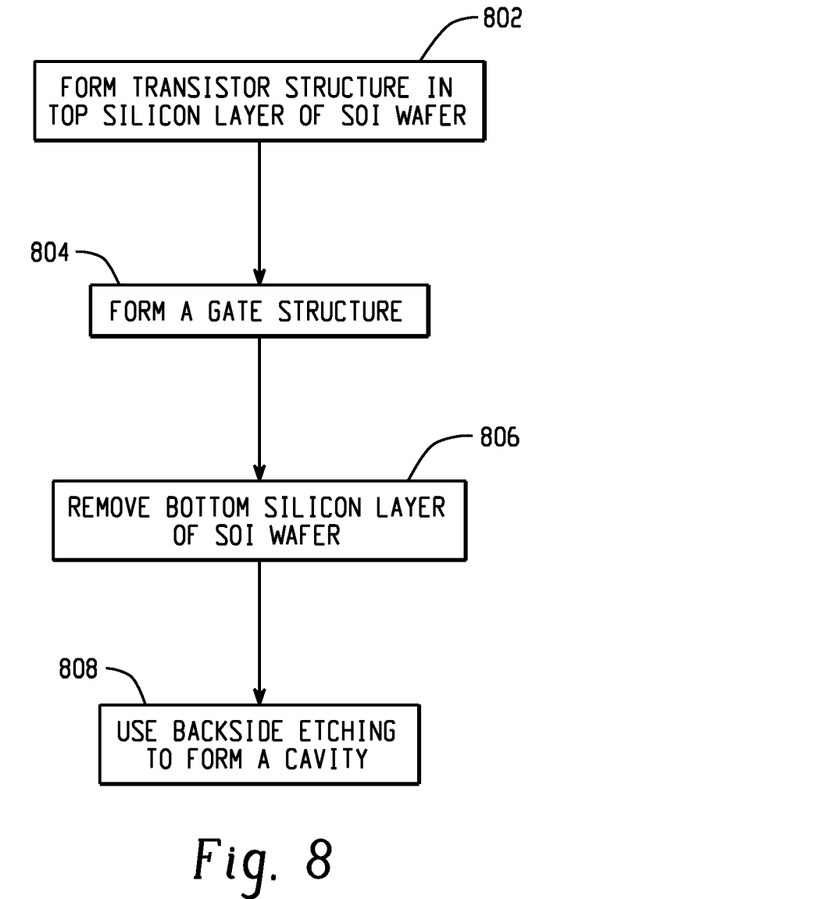
FIG. 8 depicts operations of an example method for forming a biological field-effect transistor device, in accordance with some embodiments.

FIG. 8 depicts operations of an example method for forming a biological field-effect transistor device, in accordance with some embodiments. FIG. 8 is described with reference to FIGS. 7A-7D above for ease of understanding. But the process of FIG. 8 is applicable to other structures as well. At 802, a transistor is formed in the top silicon layer of a silicon-on-insulator (SOI) wafer, the transistor including source, drain, and channel regions. An example of this is shown in FIG. 7A, which depicts the active device region 104 having a transistor formed therein. At 804, a gate of the transistor is formed. An example of this is shown in FIG. 7A, which depicts the gate 106. At 806, at least a portion of a bottom silicon layer of the SOI wafer is removed. For example, FIG. 7C shows that at least a portion of the substrate 702 shown in FIGS. 7A and 7B has been removed. At 808, a cavity is formed using a backside etching process, where the cavity comprises an opening formed in an oxide layer and a top silicon layer of the SOI wafer. An example of this cavity is the cavity 102 illustrated in FIG. 7D and other figures (e.g., FIGS. 1A-1C, 1E, 1F, 2, and 3) described above. The cavity is configured to receive one or more charged molecules. In examples, the source, drain, and channel regions of the transistor are separated from the cavity in a lateral direction, with the gate extending between the cavity and the source, drain, and channel regions. It is noted that in embodiments, some of the steps 802-808 of FIG. 8 are performed simultaneously and not necessarily sequentially, and that in embodiments, the ordering of the steps 802-808 varies from that depicted in the figure.

The present disclosure is directed to biosensor devices and methods of fabricating the same. An example biosensor device includes a cavity formed in a substrate and configured to receive one or more charged molecules. The example biosensor device also includes a transistor formed in the substrate and including a source region, a drain region, and a channel region that are spatially separated from the cavity in a lateral direction. The example biosensor device further includes a gate of the transistor disposed below the cavity and extending between the cavity and the source, drain, and channel regions. A voltage potential of the gate is based on a number of the charged molecules in the cavity.

Another example biosensor device comprises a substrate including (i) a first layer comprising a semiconductor material, and (ii) a second layer formed over the first layer and comprising a dielectric material. The biosensor device also includes a cavity comprising an opening formed in the first and second layers, the cavity being configured to receive one or more charged molecules. The biosensor device also includes a transistor formed in the first layer of the substrate and including a source region, a drain region, and a channel region that are spatially separated from the cavity in a lateral direction. A gate of the transistor is disposed below the cavity and extends between the cavity and the source, drain, and channel regions. A voltage potential of the gate is based on a number of the charged molecules in the cavity In an example method for forming a biosensor device, a transistor is formed in a top silicon layer of a silicon-on-insulator (SOI) wafer, the transistor including source, drain, and channel regions. A gate of the transistor is formed. At least a portion of a bottom silicon layer of the SOI wafer is removed. A backside etching process is used to form a cavity, the cavity comprising an opening formed in an oxide layer and the top silicon layer of the SOI wafer. The cavity is configured to receive one or more charged molecules. The source, drain, and channel regions are spatially separated from the cavity in a lateral direction, and the gate is disposed below the cavity and extends between the cavity and the source, drain, and channel regions.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A biosensor device comprising:
a substrate including (i) a first layer comprising a semiconductor material and an insulator material, and (ii) a second layer formed over the first layer and comprising a dielectric material;
a cavity that extends entirely through the first layer and the second layer of the substrate, the cavity being configured to receive one or more charged molecules;
a transistor formed in the substrate and including a source region, a drain region, and a channel region that are spatially separated from the cavity in a lateral direction by the insulator material; and
a gate of the transistor disposed below the cavity and extending between the cavity and the source, drain, and channel regions, wherein the voltage potential of the gate is based on the number of charged molecules in the cavity.

2. The biosensor device of claim 1, wherein the cavity comprises at least two sidewalls and a bottom surface, the bottom surface comprising a portion of the gate.

3. The biosensor device of claim 2, wherein the portion of the gate is configured to immobilize the one or more charged molecules.

4. The biosensor device of claim 1, wherein a current between the source and drain regions of the transistor is based on the voltage potential of the gate.

5. The biosensor device of claim 1, wherein
the first layer comprises an active semiconductor region surrounded by shallow trench isolation (STI) insulator material.

6. The biosensor device of claim 5, wherein the second layer comprises a buried oxide layer of a silicon-on-insulator (SOI) wafer, and wherein the active semiconductor region is formed in a top silicon layer of the SOI wafer.

7. The biosensor device of claim 1, wherein the gate comprises polysilicon formed below the first layer.

8. The biosensor device of claim 1, wherein the cavity comprises a dry environment, the cavity being configured to immobilize the one or more charged molecules without a fluidic solution.

9. The biosensor device of claim 1, wherein the cavity is configured to hold a fluidic solution including the one or more charged molecules.

10. A biosensor device comprising:
a substrate including (i) a first layer comprising a semiconductor material and an insulator material, and (ii) a second layer formed over the first layer and comprising a dielectric material;
a cavity comprising an opening that extends entirely through the first layer and the second layer of the substrate, the cavity being configured to receive one or more charged molecules;
a transistor formed in the first layer of the substrate and including a source region, a drain region, and a channel region that are spatially separated from the cavity in a lateral direction by the insulator material; and
a gate of the transistor disposed below the cavity and extending between the cavity and the source, drain, and channel regions, wherein the voltage potential of the gate is based on the number of charged molecules in the cavity.

11. The biosensor device of claim 10, wherein the cavity comprises at least two sidewalls and a bottom surface, the bottom surface comprising a portion of the gate.

12. The biosensor device of claim 11, wherein the portion of the gate is configured to immobilize the one or more charged molecules.

13. The biosensor device of claim 10, wherein a current between the source and drain regions of the transistor is based on the voltage potential of the gate.

14. The biosensor device of claim 10, wherein the first layer comprises an active semiconductor region surrounded by shallow trench isolation (STI) insulator material.

15. The biosensor device of claim 14, wherein the second layer comprises a buried oxide layer of a silicon-on-insulator (SOI) wafer, and wherein the active semiconductor region is formed in a top silicon layer of the SOI wafer.

16. The biosensor device of claim 10, wherein the gate comprises polysilicon formed below the first layer.

17. The biosensor device of claim 10, wherein the cavity comprises a dry environment, the cavity being configured to immobilize the one or more charged molecules without a fluidic solution.

18. A biosensor device comprising:
a substrate including (i) a first layer comprising a semiconductor material and an insulator material, and (ii) a second layer formed over the first layer and comprising a dielectric material;
a cavity that extends entirely through the first layer and the second layer of the substrate, the cavity being configured to receive one or more charged molecules;

a transistor formed in the substrate including a source region, a drain region, and a channel region that are spatially separated from the cavity by the insulator material; and a gate of the transistor disposed below the cavity and extending between the cavity and the source, drain, and channel regions.

19. The biosensor device of claim 18, wherein the generated output is indicative of a number of charged molecules present in the cavity.

20. The biosensor device of claim 18, wherein the cavity is formed using a backside etching process.

* * * * *